(12) United States Patent
Cleary et al.

(10) Patent No.: US 7,188,421 B2
(45) Date of Patent: Mar. 13, 2007

(54) ORTHODONTIC APPLIANCES HAVING A CONTOURED BONDING SURFACE

(75) Inventors: James D. Cleary, Glendora, CA (US); David K. Cinader, Yorba Linda, CA (US); Oliver L. Puttler, La Crescenta, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 444 days.

(21) Appl. No.: 10/428,255

(22) Filed: May 2, 2003

(65) Prior Publication Data
US 2004/0219473 A1 Nov. 4, 2004

(51) Int. Cl.
*B21F 43/00* (2006.01)
*A61C 3/00* (2006.01)

(52) U.S. Cl. .......................... 29/896.11; 433/8; 433/9; 433/24

(58) Field of Classification Search .................. 433/9, 433/8, 24
See application file for complete search history.

(56) References Cited

U.S. PATENT DOCUMENTS

| | | | |
|---|---|---|---|
| 4,551,096 A | 11/1985 | Dellinger | |
| 4,657,508 A | 4/1987 | Dellinger | |
| 5,015,180 A | 5/1991 | Randklev | |
| 5,172,809 A | 12/1992 | Jacobs et al. | |
| 5,354,199 A | 10/1994 | Jacobs et al. | |
| 5,429,229 A | 7/1995 | Chester et al. | |
| 5,971,754 A * | 10/1999 | Sondhi et al. | 433/24 |
| 6,126,443 A | 10/2000 | Burgio | |
| 6,142,780 A | 11/2000 | Burgio | |
| 6,302,688 B1 | 10/2001 | Jordan et al. | |
| 6,358,044 B1 | 3/2002 | Andreiko | |
| 6,386,865 B1 | 5/2002 | Suh et al. | |
| 6,607,382 B1 | 8/2003 | Kuo et al. | |

(Continued)

FOREIGN PATENT DOCUMENTS

WO    WO 01/85047    11/2001

(Continued)

OTHER PUBLICATIONS

Morita Europe, Demonstration Models, Apr. 24, 2003, www.jmoritaeurope.de/DemomodelsEng.html, 8 pages.

(Continued)

*Primary Examiner*—Cris L. Rodriguez
*Assistant Examiner*—Candice C. Stokes
(74) *Attorney, Agent, or Firm*—James D. Christoff

(57) ABSTRACT

A quantity of a photocurable composition, such as an orthodontic adhesive containing a photoinitiator, is placed between the base of an orthodontic appliance and a replica of a patient's tooth structure. The replica is made using a material that transmits actinic radiation. As the appliance is pressed into firm contact with the replica tooth structure, an outer surface of the photocurable composition assumes the configuration of the underlying portion of the replica tooth structure. Actinic radiation is then directed to the photocurable composition, and at least part of the actinic radiation is directed through the replica tooth model in order to harden the photocurable composition. The hardened composition provides a contoured bonding surface having a shape that matches corresponding regions of the patient's tooth structure. Methods are also disclosed for making an orthodontic indirect bonding transfer apparatus for use with appliances having a contoured bonding surface.

16 Claims, 4 Drawing Sheets

U.S. PATENT DOCUMENTS 6,705,863 B2   3/2004   Phan et al.
6,743,013 B2 * 6/2004   Jordan et al. .................. 433/9

FOREIGN PATENT DOCUMENTS

WO      WO 02/089693      11/2002

OTHER PUBLICATIONS

Moskowitz et al., A New Look at Indirect Bonding, Journal of Clinical Orthodontics, 1996, vol. XXX No. 5, pp. 277-281.

Hickham, Predictable Indirect Bonding, Journal of Clinical Orthodontics, 1993, vol. XXVII, No. 4, pp. 215-217.

Sinha et al., A Thermal-Cured Fluoride-Releasing Indirect Bonding System, Journal of Clinical Orthodontics, 1995, vol. XXIX, No. 2, pp. 97-100.

Cooper et al., Indirect Bonding with Adhesive Precoated Brackets, Journal of Clinical Orthodontics, Mar., 1993, vol. XXVII, No. 3, pp. 164-167.

Models Plus, "Education Through Innovation", Product Catalog.

* cited by examiner

ORTHODONTIC APPLIANCES HAVING A CONTOURED BONDING SURFACE

BACKGROUND OF THE INVENTION

1. Field of the Invention

This invention broadly relates to methods and apparatus for making orthodontic appliances such as brackets and buccal tubes. More particularly, the present invention concerns orthodontic appliances having a bonding surface for attachment to a tooth, and the bonding surface is shaped as desired in accordance with the selected treatment objectives. The present invention also concerns indirect bonding transfer apparatus that includes one or more appliances having a contoured bonding surface.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion while eating.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In the past, metallic orthodontic appliances including brackets and buccal tubes were often welded to bands. Each band was adapted to encircle one of the patient's teeth and provide a secure connection between the tooth and the appliance. Typically, a composition such as a band cement was applied to the inner surface of the band before placement on the tooth in order to fill any gaps or voids between the band and the tooth enamel and help prevent the band from "rocking" on the tooth.

However, metallic bands are generally considered unaesthetic and contribute to an undesirable "metallic mouth" appearance. Moreover, for a proper fit, each band must be carefully selected so that its size and shape match the size and shape of the patient's tooth. Additionally, bands are not considered suitable for use with appliances made of non-metallic materials, such as ceramic and plastic.

In recent years, there has been great interest in the use of appliances that are bonded to the enamel surface of the teeth by an adhesive. These appliances are not mounted on metallic bands and consequently the patient's appearance is improved. In addition, the expense of the bands, as well as the time needed to select the bands and attach the appliances to the bands, can be avoided.

However, it is important that any appliance that is adhesively bonded to a tooth remain firmly attached to the tooth over the entire course of treatment. Orthodontic appliances are sometimes subject to significant forces in the oral cavity due to the presence of a food object that may be located between the appliances and the teeth during mastication. These forces can be relatively large when the patient is chewing a relatively hard food object such hard candy or ice, and may in some instances cause the appliance to debond from the tooth.

Unfortunately, the progress of the orthodontic treatment program can come to an abrupt halt when an orthodontic appliance unintentionally debonds from a tooth. In that event, the patient should immediately return to the practitioner for re-attachment or replacement of the appliance so that treatment can resume. The time and expense of both the practitioner and the patient that is incurred to respond to a spontaneously debonded appliance is considered a nuisance that is best avoided.

As a result, manufacturers of orthodontic appliances often go to great lengths to ensure that their appliances remain firmly adhered to the teeth over the entire course of treatment. To this end, the base of the appliances is often provided with features to improve the strength of the bond between the appliance and the tooth. As one example, the base may have a concave, compound contour that closely matches the convex, compound surface of the tooth so that a mating fit is obtained. As another example, the base may include mechanical or chemical features such as projections, recesses or chemical treatments that serve to enhance the strength of the bond between the adhesive and the appliance. However, appliances are typically manufactured and sold with bases having a shape that matches the expected shape of a statistical "average" patient, which may or may not be similar in shape to the tooth of the particular patient undergoing treatment.

In addition, in many types of orthodontic techniques, the shape of the appliance base is an important factor for helping to ensure that the teeth move to their intended final positions. For example, one common type of orthodontic treatment technique is known as the "straight-wire" technique, where the resilient archwire tends to follow a smooth curve that lies in a horizontal plane at the conclusion of treatment. If, for instance, the convex shape of the patient's tooth is oriented in a direction that is different than the orientation of the concave shape of an appliance made for an "average" patient, the appliance will not be properly oriented to the tooth and the archwire slot will extend at an improper angle relative to the tooth for straight-wire treatment. As the archwire assumes a level, straight configuration near the end of the treatment program, the improperly oriented appliance will cause the tooth to assume a corresponding, improper position.

Other aspects of the shape of the appliance base are also important. For example, it may be desirable to provide a base having a "wedge-shaped" configuration, so that the long axis of the tooth is pivoted or tipped toward a certain pre-selected orientation as the archwire assumes the configuration of a smooth, horizontal curve near the end of the treatment program. In this regard, it is possible to orient the shape of the wedge so that the tooth is pivoted in a rotational direction about its long axis, or alternatively so that the long axis of the tooth is tipped along either a mesial-distal reference axis or a labial-lingual reference axis.

In general, orthodontic appliances that are adapted to be adhesively bonded to the patient's teeth are placed on the teeth by either one of two methods: a direct bonding method, or an indirect bonding method. In the direct bonding method, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place. Typical adhesives include light-curable adhesives that begin to harden upon exposure to actinic radiation, and two-component chemical-cure adhesives that begin to harden when the components are mixed together.

While the direct bonding technique described above is in widespread use and is considered satisfactory by many, there are shortcomings that are inherent with such a technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally bumped from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some time may be necessary before the practitioner is satisfied with the location of each appliance. At the same time, however, the patient may experience discomfort and have difficulty in remaining relatively motionless, especially if the patient is an adolescent. As can be appreciated, there are aspects of the direct bonding technique that can be considered a nuisance for both the practitioner and for the patient.

Indirect bonding techniques often avoid many of the problems noted above. In general, indirect bonding techniques known in the past have involved the use of a transfer tray having a shape that matches the configuration of at least part of a patient's dental arch. A set of appliances such as brackets are releasably connected to the tray at certain, predetermined locations. Adhesive is applied to the base of each appliance, and the tray is then placed over the patient's teeth until such time as the adhesive hardens. Next, the tray is detached from the teeth as well as from the appliances, with the result that all of the appliances previously connected to the tray are now bonded to the respective teeth at their intended, predetermined locations.

In more detail, one method of indirect bonding of orthodontic appliances includes the steps of taking an impression of each of the patient's dental arches and then making a replica plaster or "stone" model from each impression. Optionally, a soap solution (such as Model Glow brand solution from Whip Mix Corporation) or wax is applied to the stone model. A separation solution (such as COE-SEP brand tinfoil substitute from GC America, Inc.) is then applied to the stone model and allowed to dry. If desired, the teeth of the model can be marked with a pencil to assist in placing the brackets in ideal positions.

Next, the brackets are bonded to the stone models. Optionally, the bonding adhesive can be a chemical curing adhesive (such as Concise brand adhesive from 3M) or a light-curable adhesive (such as Transbond XT brand adhesive or Transbond LR brand adhesive, from 3M). Optionally, the brackets may be adhesive precoated brackets such as those described in U.S. Pat. Nos. 5,015,180, 5,172,809, 5,354,199 and 5,429,229.

A transfer tray is then made by placing a matrix material over the model as well as over the brackets placed on the model. For example, a plastic sheet matrix material may be held by a frame and exposed to radiant heat. Once the plastic sheet material has softened, it is placed over the model and the brackets. Air in the space between the sheet material and the model is then evacuated, and the plastic sheet material assumes a configuration that precisely matches the shape of the replica teeth of the stone model and the attached brackets.

The plastic material is then allowed to cool and harden to form a tray. The tray and the brackets (which are embedded in an interior wall of the tray) are then detached from the stone model and sides of the tray are trimmed as may be desired. Typically, the adhesive that previously attached the brackets to the stone models remains connected to the brackets. This adhesive has an outer surface that subsequently provides a bonding surface for attaching the brackets to the patient's teeth in the oral cavity. In some instances, this bonding surface will have a contoured shape that roughly matches the shape of the replica tooth structure as well as the patient's tooth structure.

Once the patient has returned to the office, a quantity of adhesive is placed on the base of bracket, and the tray with the embedded brackets is then placed over the matching portions of the patient's dental arch. Since the configuration of the interior of the tray closely matches the respective portions of the patient's dental arch, each bracket is ultimately positioned on the patient's teeth at precisely the same location that corresponds to the previous location of the same bracket on the stone model.

Both light-curable adhesives and chemical curing adhesives have been used in the past in indirect bonding techniques to secure the brackets to the patient's teeth. If a light-curable adhesive is used, the tray is preferably transparent or translucent. If a two-component chemical curing adhesive is used, the components can be mixed together immediately before application of the adhesive to the brackets. Alternatively, one component may be placed on each bracket base and the other component may be placed on the tooth surface. In either case, placing of the tray with the embedded brackets on corresponding portions of the patient's dental arch enables the brackets to be bonded to the teeth as a group using only a short amount of time that the patient is occupying the chair in the operatory. With such a technique, individual placement and positioning of each bracket in seriatim fashion on the teeth is avoided.

A variety of transfer trays and materials for transfer trays have been proposed in the past. For example, some practitioners use a soft sheet material (such as Bioplast tray material from Scheu-Dental GmbH) for placement over the stone model and the appliances on the model. A vacuum is applied to draw the soft material into intimate contact with the model and the appliances on the model. Next, a stiffer sheet material (such as Biocryl sheet material, from Scheu-Dental GmbH or Great Lakes Orthodontics, Ltd.) is formed over the softer sheet material, again using a vacuum forming technique. The stiffer material provides a backbone to the tray, while the softer material initially holds the appliances and yet is sufficiently flexible to release from the appliances after the appliances have been fixed to the patient's teeth.

It has also been proposed in the past to use a silicone impression material or a bite registration material (such as Memosil 2, from Heraeus-Kulzer GmbH & Co. KG). The silicone material is applied over the appliances that are attached to the study model so that the appliances are partially encapsulated.

In an article entitled "*A New Look at Indirect Bonding*" by Moskowitz et al. (*Journal of Clinical Orthodontics, Volume XXX, Number 5*, May 1996, pages 277 et sec.), a technique for making indirect bonding trays is described using Reprosil impression material (from Dentsply International). The impression material is placed with a syringe over brackets that have been previously placed on a stone model. Next, a sheet of clear thermoplastic material is drawn down over the impression material using a vacuum-forming technique. The resultant transfer tray is then removed from the model for subsequent placement on the patient's dental arch.

Indirect bonding techniques offer a number of advantages over direct bonding techniques. For one thing, and as indicated above, it is possible to bond a plurality of brackets to a patient's dental arch simultaneously, thereby avoiding the need to bond each appliance in individual fashion. In addition, the indirect bonding tray helps to locate all of the brackets in their proper, intended positions such that adjustment of each bracket on the surface of the tooth before bonding is avoided. The increased placement accuracy of the appliances that is often afforded by indirect bonding techniques helps ensure that the patient's teeth are moved to their proper, intended positions at the conclusion of treatment.

While the indirect bonding techniques as described above have proven satisfactory for many practitioners, there is a continuing need to improve the state of the art. Moreover, there is a need to improve methods and apparatus for providing an appliance with a bonding surface that is especially adapted for the particular patient at hand.

SUMMARY OF THE INVENTION

The present invention relates to an orthodontic appliance with an improved bonding surface as well as methods and apparatus for making the same. The bonding surface of the present invention is made of a light-curable composition that is cured to a relatively hard condition simultaneously across its entire extent, even when the appliance is made of a material that is opaque to the transmission of actinic radiation. In addition, the bonding surface is relatively smooth, even in regions near the center of the appliance base. As a result, a bonding surface having a precise, mating fit with the shape of the patient's tooth structure is readily achieved.

The present invention is carried out by use of a model that transmits actinic radiation. Some of the actinic radiation that passes through the model will reach portions of the light-curable composition that are located near the center of the appliance base. Those portions are hardened to substantially the same extent as remaining portions of the light-curable composition. Consequently, the shape of those central portions is not disturbed as the appliance is detached from the replica, and the bonding surface has a configuration that precisely matches the shape of the tooth.

In more detail, the present invention in one aspect relates to a method of making a bonding surface for an orthodontic appliance comprising:

providing a replica of a patient's tooth structure, wherein the replica is comprised of a material that transmits actinic radiation;

placing a photocurable composition on the base of at least one orthodontic appliance;

engaging the photocurable composition of each appliance with the replica tooth structure; and directing actinic radiation to the photocurable composition, wherein the act of directing actinic radiation to the photocurable composition is carried out by directing at least a portion of the actinic radiation through the replica tooth structure.

The present invention is also directed in another aspect to a method of making orthodontic transfer apparatus for indirect bonding. This method comprises:

making a replica of a patient's tooth structure, wherein the replica is comprised of a material that transmits actinic radiation;

placing a photocurable composition on the base of at least one orthodontic appliance;

engaging the photocurable composition of each appliance with the replica tooth structure;

directing actinic radiation to the photocurable composition, wherein the act of directing actinic radiation to the photocurable composition is carried out at least in part by directing actinic radiation through the replica of the patient's tooth structure; and forming a transfer apparatus over each appliance and the replica tooth structure.

The present invention is also directed to an apparatus for making a bonding surface for an orthodontic appliance. The apparatus comprises a replica of tooth structure, wherein the replica is made of a material that transmits actinic radiation. The apparatus also includes an orthodontic appliance and a photocurable composition between the appliance and the replica. The apparatus additionally includes a source of actinic radiation that is operable to direct at least a portion of the actinic radiation along a path through the replica and toward the photocurable composition.

These and other aspects of the invention are described in more detail below and are illustrated in the accompanying drawings.

DETAILED DESCRIPTION OF THE PREFERRED EMBODIMENTS

Figure 1:
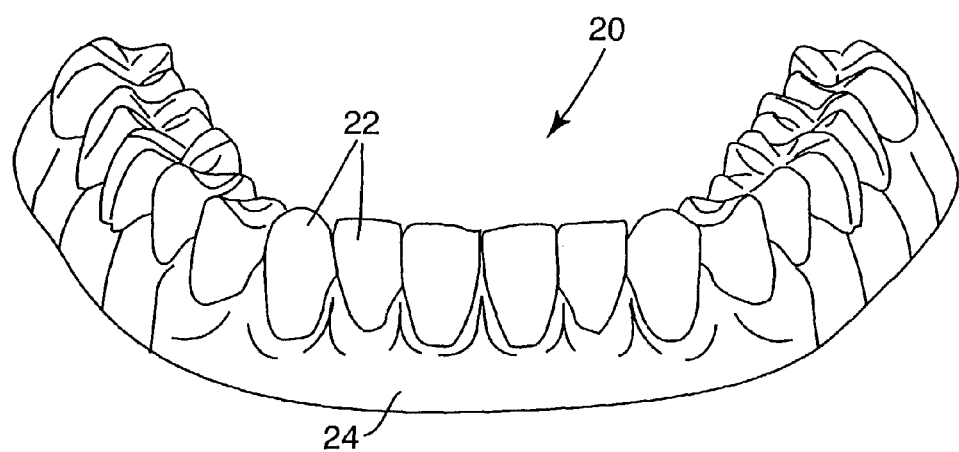
FIG. 1 is a top and front view showing a physical replica of one dental arch of an orthodontic patient, illustrating an example of a replica of a patient's tooth structure and adjacent gingival tissue as they might appear before the commencement of treatment.

A method for indirect bonding of one or more orthodontic appliances in accordance with one aspect of the present invention will first be described. FIG. 1 illustrates a positive replica 20 of a portion of a dental arch of an orthodontic patient. For exemplary purposes, the replica 20 represents the patient's lower dental arch. However, a replica of a patient's upper dental arch may be provided as an addition to or as an alternative to the lower dental arch replica as shown. As a further option, the replica 20 may represent only a portion of a dental arch, such as a quadrant of an arch or only one or two teeth of a dental arch. In the example illustrated, the replica 20 includes a number of replica teeth 22, corresponding to each tooth of the patient's lower dental arch.

Optionally, the replica 20 is made by first taking an impression of the patient's lower dental arch, using care to avoid undue distortion. Examples of suitable impression material include hydrocolloid impression materials and vinyl polysiloxane impression materials (such as Position Penta brand vinyl polysiloxane impression material from 3M ESPE). In some cases, and depending upon the type of material used to make the replica, an alginate impression material may be used such as Unijel II brand alginate impression material from 3M Unitek.

The model or replica 20 is then made from the impression. As an option, the replica 20 includes only the replica teeth 22 and sufficient replica gingival tissue 24 to hold the replica teeth 22 together.

The replica 20 including the replica teeth 22 are made from a material that transmits actinic radiation. Suitable materials include epoxy resins that are transparent or translucent when hardened. Preferably, the material is optically clear and nonporous. An example of a suitable epoxy is E-CAST F-82 clear epoxy resin and No. 302 (or No. UCE-302) hardener, from United Resin Corporation. Other suitable materials include polyesters and urethanes.

Care is taken during making of the replica 20 to avoid the presence of bubbles and/or small voids. If small voids are present, the voids can be filled with an additional quantity of material that transmits actinic radiation.

As an alternative, the replica 20 may be made using digital data that is representative of the patient's teeth and adjacent gingival tissue. The digital data may be obtained by use of a hand-held intra-oral scanner or other device known in the art. As another option, the digital data may be obtained by scanning an impression or a stone model. The replica 20 may then be made from the digital data using, for example, a stereo lithographic printer and a material that transmits actinic radiation.

The replica 20 may also be made using digital data in conjunction with a milling process. For example, a CNC milling machine, similar to the CAD/CIM milling machines sold by Cerec Network of Buelach, Switzerland, may be used to mill replicas made of ceramic, composite or other materials. An intra-oral camera, similar to the cameras associated with the Cerec machines, may be used to obtain digital data representing the shape of the dental arches. Alternatively, a scanner may be used to scan an impression or a model of an impression to obtain the digital data.

Preferably, the replica 20 is an accurate representation of the patient's oral structure. In particular, the replica teeth 22 will have a configuration and orientation that is identical to the configuration and orientation of the corresponding teeth of the orthodontic patient. In addition, the replica gingival tissue 24 will have a shape that matches the shape of the corresponding portions of the gingival tissue of the patient.

Figure 2:
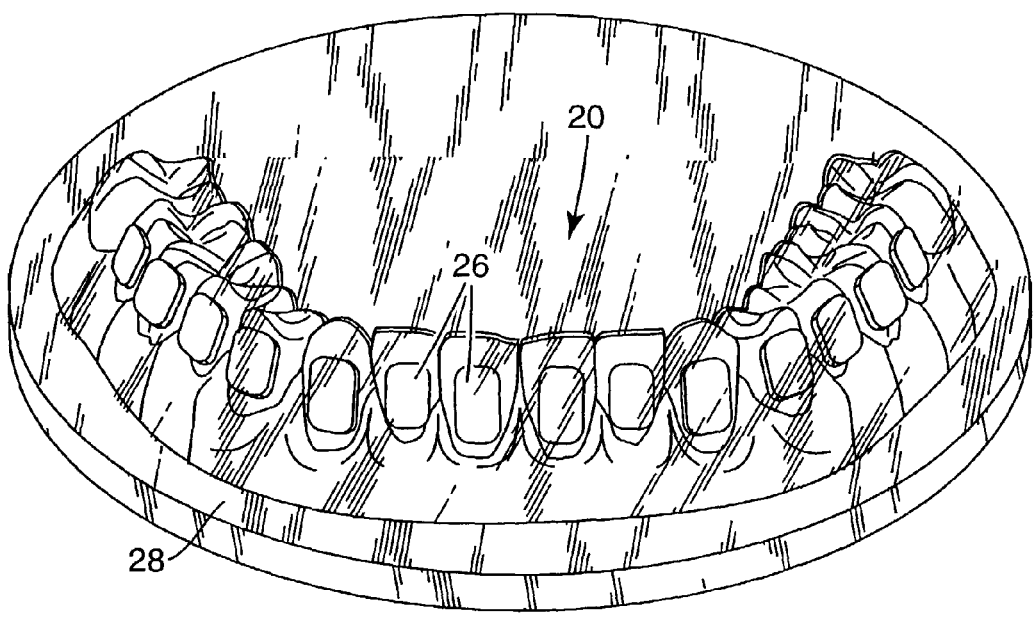
FIG. 2 is a view of the dental arch replica shown in FIG. 1, along with spacer material that has been applied to the replica.
Figure 3:
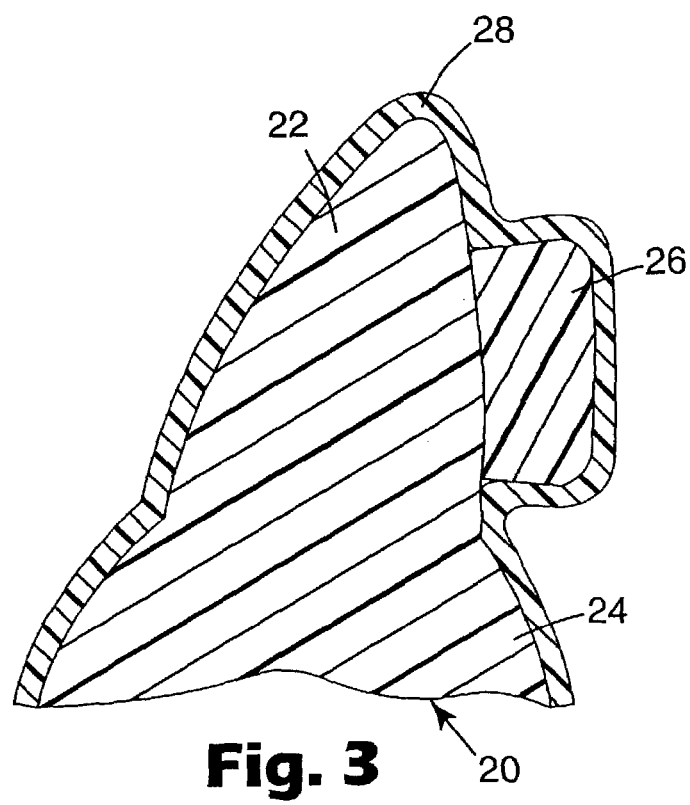
FIG. 3 is an enlarged side cross-sectional view of one of the replica teeth illustrated in FIG. 2 along with the spacer material.

Next, and as shown in FIGS. 2 and 3, a spacer material is applied to the replica 20. In this example, the spacer material includes a first spacer material 26 that comprises a series of discrete dabs or pre-formed segments of material that are placed at approximate, pre-determined locations on the replica teeth 22. Each of the dabs or segments of spacer material 26 is placed in a location that corresponds to a subsequent location of an orthodontic appliance and has an overall size that is at least as large as the selected appliance. For instance, each of the segments of spacer material 26 is placed in a location corresponding to the facial axis point (or "FA" point) of the corresponding tooth, although other locations are also possible. As will be described below, each of the segments of spacer material 26 functions to subsequently provide clearance in the transfer apparatus for receiving an orthodontic appliance.

As an alternative to segments of spacer material 26, the spacer material 26 may instead have a elongated configuration in the form of a strip. The strip has sufficient length to extend across at least some, and preferably all, of the replica teeth 22, following a path that corresponds to a subsequent position of an archwire. The strip has sufficient width to provide clearance for each of the appliances that is subsequently affixed to the archwire. In practice, spacer material in the shape of a strip may be preferred in instances where the teeth are in general alignment (as the teeth appear in FIG. 1), while the spacer material in the shape of discrete segments or dabs may be preferred in instances where the teeth are substantially crooked and/or out of substantial alignment with each other.

In this embodiment, the spacer material also includes a sheet of spacer material 28 that preferably extends across a substantial portion of the surfaces of the replica teeth 22 and preferably across at least a portion of the surface of the replica gingival tissue 24. As illustrated in FIG. 3, the sheet spacer material 28 also extends over the segments of spacer material 26. In the illustrated example, the sheet of spacer material 28 extends over the entire buccolabial surface area of the replica teeth 22, along the occlusal edge of the replica teeth 22 and across the entire lingual side of the replica teeth 22, although other constructions are also possible.

As another alternative, the spacer material 26, 28 may be provided as an integral unitary section of material, such that separate handling of the two materials is avoided. Additionally, the sheet of material 28 (whether alone, or whether integral with the spacer material 26) may be preformed to a configuration that approximates the shape of a dental arch. Such construction facilitates subsequent conforming of the sheet 28 to the replica teeth 22 as will be described below.

The spacer material 26, 28 can be any one of a number of materials. A suitable material is a silicone material, such as "RTV 615" from General Electric. Optionally, the spacer material 26 may be temporarily held in place on the replica 20 by use of an adhesive, such as a pressure sensitive adhesive. Optionally, the segments or strips of spacer material 26 may be preformed, coated with a layer of pressure sensitive adhesive on one side and initially connected to a sheet of release material until such time as it is needed for use. Alternatively, dabs of spacer material may be provided by dispensing a quantity of flowable, hardenable material from a syringe and then shaping each dab as needed with a hand instrument.

Next, a vacuum is applied to the replica 20 and the spacer material 26, 28 in order to form the sheet of spacer material 28 to the configuration of the replica teeth 22 and gingival tissue 24. As used herein, the term "vacuum" is not necessarily limited to an absolute vacuum, and shall be understood to mean any pressure that is lower than atmospheric. In practice, the replica 20 along with the spacer material 26 is placed on a disc-shaped support having channels communicating with the vacuum pump. The sheet of spacer material 28 is then placed over the replica and the vacuum pump is activated to draw down the sheet of spacer material 28 into tight, matching conformance with the shape of the replica teeth 22 and gingival tissue 24.

Figure 4:
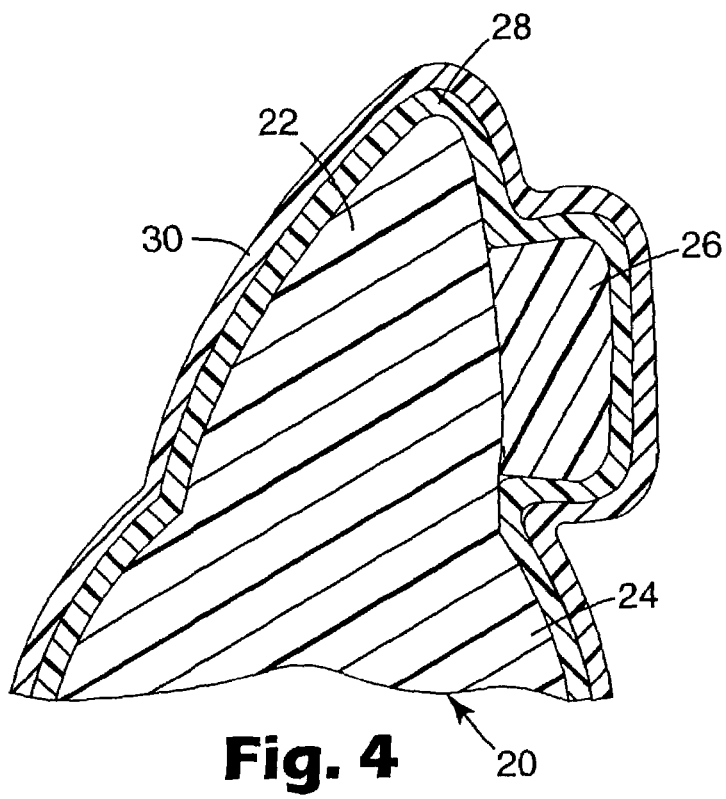
FIG. 4 is a view somewhat similar to FIG. 3, additionally showing a tray that has been formed over the spacer material.

Subsequently, a tray 30 is formed over the spacer material 26, 28 as illustrated in FIG. 4. Preferably, the tray 30 is shaped by vacuum forming a sheet of material over the sheet of spacer material 28. A suitable material for the tray 30 is a sheet of polycarbonate such as Makrolon brand material from Bayer or Lexan brand polycarbonate from GE having a thickness of 0.06 inch. Other materials, such as polyethyleneterephthalate glycol ("PETG") may also be used. Heat is applied during the vacuum forming process in order to facilitate conformance of the sheet to the configuration of the sheet of spacer material 28.

Once the tray 30 has hardened, the tray 30 is detached from the spacer material 26, 28. The spacer material 26, 28 is then detached from the replica 20 and set aside. Excess portions of the tray 30 may be trimmed as desired.

A thin layer of a release agent is then applied to the replica 20 and allowed to dry. An example of a suitable release agent is a water soluble polyvinyl alcohol, such as "PA0810" from PTM & W Company of Santa Fe Springs, Calif.

Next, a determination is made of the proper intended position of each appliance on the replica teeth 22, corresponding to the ultimate desired position of the same appliance on the patient's corresponding tooth. A variety of methods are available for determining appliance position. For example, the practitioner, practitioner's assistant or lab technician may make a pencil mark across the labial surface of each replica tooth 22. The pencil mark is preferably made with the assistance of a height gauge such as the MBT™ bracket positioning gauge or the Boone bracket positioning gauge, both from 3M Unitek Corporation. The pencil line is drawn across the labial surface of each replica tooth 22 to serve as a location guide for placement of the archwire slot of each orthodontic appliance (such as an orthodontic bracket).

Figure 5:
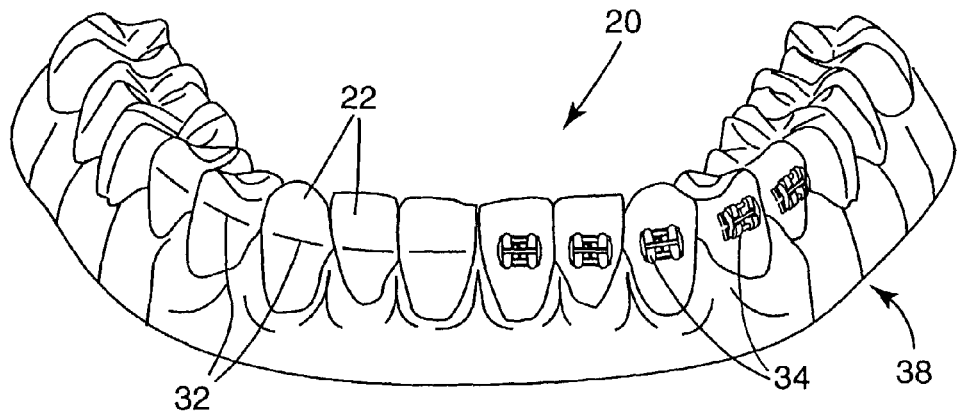
FIG. 5 is a view of the tooth structure replica illustrated in FIG. 1 after the spacer material and the tray have been removed, and additionally showing a number of orthodontic appliances that have been placed in predetermined positions on the replica.

For example, and for the replica 20 representing the patient's lower dental arch, pencil lines may be drawn parallel to the occlusal plane according to one treatment technique at a distance of 3.5 mm from the occlusal edge of the replica anterior teeth 22. Similar lines are drawn at a distance of 4.0 mm from the occlusal edge of the replica lower cuspid teeth 22 and the replica lower bicuspid teeth 22. Lines are also drawn parallel to the occlusal plane at a distance of 3.5 mm from the occlusal edge of each replica molar tooth 22 (unless the corresponding tooth of the patient will receive an appliance that is mounted on a band). In FIG. 5, some of the pencil lines as described above are designated by the numeral 32.

Next, orthodontic appliances 34 (such as orthodontic brackets and buccal tubes) as selected by the practitioner are placed on the corresponding replica teeth 22, preferably in positions such that the archwire slot of each appliance 34 is approximately aligned with the respective pencil line 32. Before each appliance 34 is placed on the respective replica tooth 22, a quantity of a composition is placed between each appliance and the corresponding tooth 22. Preferably, the composition is a light curable composition such as an orthodontic adhesive containing a photoinitiator, and the adhesive is coated across the base of each appliance 34.

Preferably, the appliances 34 are adhesive precoated appliances that have a layer of light-curable adhesive applied by the manufacturer to the base of each appliance 34. Such adhesive coated appliances are described in U.S. Pat. Nos. 5,015,180, 5,172,809, 5,354,199 and 5,429,229, all of which are assigned to the assignee of the present invention. The appliances 34 may be made of any suitable material such as metal (e.g., stainless steel), ceramic (e.g., translucent polycrystalline alumina) or plastic (e.g., translucent polycarbonate).

If the appliances 34 are not precoated with adhesive by the manufacturer, a coating of adhesive may be applied by the practitioner to the base of each appliance 34. Suitable adhesives include composites, compomers, glass ionomers and resin-modified glass ionomers. Examples of light-curable adhesives include Transbond XT brand or Transbond LR brand adhesives from 3M Unitek. Examples of chemical curing adhesives include Concise brand adhesive and Multi-Cure brand glass ionomer cement from 3M Unitek.

Once the appliances 34 have been placed on the replica teeth 22, the appliances 34 are shifted mesial-distally as needed to align the central occlusal-gingival axis of the appliance 34 with the long axis of each replica tooth 22. The appliances 34 are also shifted in an occlusal or gingival direction as needed in order to place the archwire slot of each bracket directly over the underlying pencil line 32. Optionally, a gauge such as the MBT™ gauge or Boone bracket positioning gauge mentioned above is used again to precisely position the archwire slot of each appliance 34 the distance specified above from the occlusal edge of the corresponding replica tooth 22.

Next, the practitioner applies firm pressure to each appliance 34, preferably by using a scaler or other hand instrument to apply force to the archwire slot of each appliance 34 in order to ensure that the appliance 34 is firmly seated on the replica tooth 22. A tool such as a dental explorer is then used to remove any adhesive flash that may have been extruded near the periphery of the base of the appliance 34 during seating.

Figure 6:
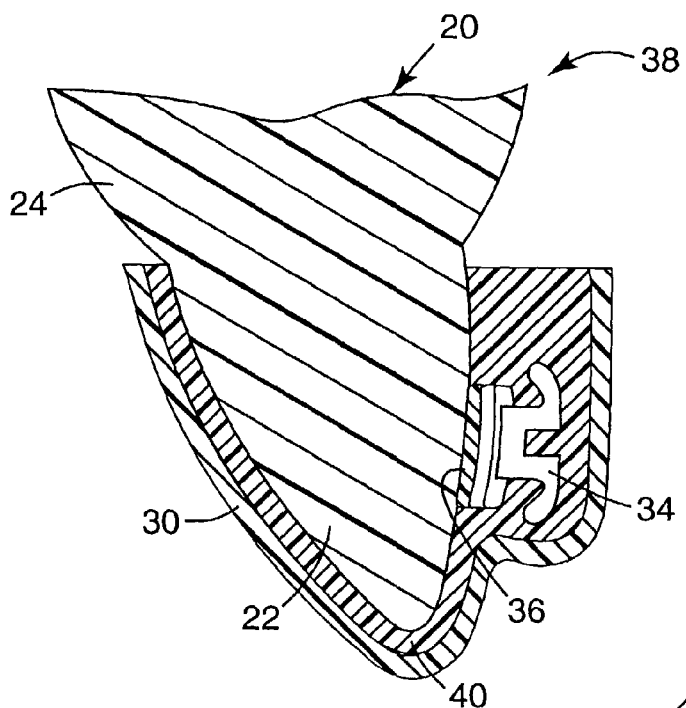
FIG. 6 is an enlarged side cross-sectional view of one of the replica teeth and appliances depicted in FIG. 5, and additionally showing a quantity of matrix material which has been placed between the replica and the tray shown in FIG. 4 after the replica and the tray have been inverted to make a transfer apparatus.

The adhesive is designated by the numeral 36 in FIG. 6 and is not necessarily drawn to scale. The use of a light curable adhesive 36 is advantageous since an orthodontist's assistant or a lab technician can carry out the steps described immediately above and then give the replica 20 to the orthodontist or to a lab supervisor. The orthodontist or supervisor may then make a final check as to the precise placement of each appliance 34 on the corresponding replica tooth 22 before the adhesive 36 has hardened. As one example, a number of replicas 20 may be prepared by the assistant or technician and stored in an opaque container such as a black plastic box until reviewed by the orthodontist or supervisor. In this manner, the orthodontist or supervisor can review the placement of the appliances 34 on a number of different replicas 20 at a convenient time without undue or premature curing of the adhesive 36.

Once the accuracy of the appliance position has been confirmed, a source of actinic radiation is activated in order to direct actinic radiation toward the adhesive 36. As the actinic radiation reaches the adhesive, the photopolymerization reaction is initiated and the adhesive 36 hardens. Suitable sources of actinic radiation include hand-held light curing units as well as stationary curing chambers.

An example of a suitable curing chamber is the Triad 2000 brand visible light curing system from Dentsply. Preferably, the curing chamber is sufficiently large to contain a number of replicas 20 so that the adhesive 36 on a number of replicas 20 can be cured simultaneously. In such a chamber, the light source and the replicas 20 preferably move relative to each other during energization of the light source to facilitate curing of each portion of the adhesive 36.

If the appliances 34 are made of metal or other opaque material, it is preferable to expose the replica 20 to the curing light for a relatively long amount of time such as 3 to 5 minutes to ensure that the adhesive 36 has sufficiently hardened. As an alternative to the light curing chambers mentioned above, a hand-held curing unit may be used, such as Ortholux XT brand curing unit from 3M Unitek.

The use of transparent or translucent materials to make the replica 20 is especially advantageous in instances where the appliances 34 are made of opaque materials, since the actinic radiation can be transmitted through the replica 20 for curing portions of the adhesive 36 that are located adjacent the middle of the appliance base. Those portions might otherwise not receive sufficient actinic radiation to enable the adhesive to harden to a satisfactory extent. Actinic radiation can include wavelengths in the visible range (i.e., about 400 nm to about 750 nm), ultraviolet range (i.e., about 4 nm to about 400 nm), infrared range (i.e. about 750 nm to about 1000 micrometers) or any combination thereof, in accordance with the type of initiator contained in the adhesive 36.

Actinic radiation passing through the replica 20 may travel along one or more different paths. For example, the actinic radiation may be emitted from a source that is located on the lingual side of the replica 20 directly opposite the appliance and travel in a buccolabial direction toward the appliance base. As another example, the source of actinic radiation may be offset from a position directly opposite the appliance, and positioned such that the actinic radiation follows along a path that extends at an angle relative to a buccolabial-lingual reference axis. As used herein, a path "through" the replica is not limited to paths that enter and exit on opposite sides of the replica, and also include paths that enter and exit on the same side of the replica.

Additionally, the replica 20 need not consist entirely of a material that transmits actinic radiation. For example, the replica 20 may include a core or other section that is made of a material opaque to actinic radiation, and a layer of a light-transmitting material is then applied over the core or other section. In that instance, a layer of reflective material may be placed between the layer of light-transmitting material and the core or other section in order to facilitate the passage of actinic radiation to the adhesive 36.

The appliances 34 may be placed on the replica teeth 22 by means of robotic equipment as an alternative to the placement by hand as described above. For example, the robotic equipment may include a gripping arm that is programmed to pick an appropriate appliance 34 from a set of appliances and place the selected appliance on the appropriate replica tooth 22. The robotic arm then proceeds to grasp another appliance 34 for placement on another replica tooth 22.

Optionally, the path of movement of the robotic arm and the ultimate position of the placed appliance 34 are determined by computer software that has access to digital data representing a virtual model of the replica 20. The software preferably includes subprograms suitable to analyze the existing malocclusion of the patient and select proper appliances for treatment of the particular malocclusion at hand. Optionally, the software enables the practitioner, patient or other observer to see on a monitor or other video output a virtual representation of the patient's teeth as they should appear at the conclusion of treatment using the selected appliances placed on certain locations of the teeth.

Preferably, the software includes subprograms for selecting appliances, analyzing malocclusions and/or predicting tooth movement and final positions of the teeth. An example of software for choosing appliances is described in pending U.S. patent application Ser. No. 10/081,220 entitled "Selection of Orthodontic Brackets", the disclosure of which is expressly incorporated by reference herein. Optionally, the software includes subprograms for making custom orthodontic appliances using, for example, a computer numerical control milling machine, instead of selecting appliances from an existing set of appliances as mentioned above.

As an additional option, an orthodontic archwire may be placed in the slots of the appliances 34 and ligated in place. This step serves to further reduce the patient's time that is subsequently spent in the chair.

The replica 20, together with the appliances 34 (and the archwire, if any), represent a treatment model 38 of an orthodontic patient set-up as shown in FIG. 5. A matrix material is then applied, either to the model 38 or to the channel of the tray 30. For example, if the matrix material is relatively viscous and resembles a semi-liquid or gel, the matrix material may be applied to the model 38 as it appears in FIG. 5, using a syringe, brush or other technique. Alternatively, if the matrix material has a relatively low viscosity and resembles a liquid, it may be preferable to invert the tray 30 such that the open side of the channel of the tray 30 is facing upwardly as shown in FIG. 6. If the tray 30 is inverted, the tray 30 is not initially trimmed along the outermost distal sides (corresponding to the ends of the dental arch) so that the liquid matrix material is contained within the tray channel.

Subsequently, the model 38 is positioned in the tray 30 such that the matrix material is received in the channel of the tray 30 and between the tray 30 and the model 38. In FIG. 6, the matrix material is designated by the numeral 40 and surrounds the appliance 34 as well as the labial and lingual surfaces of the replica tooth 22. The matrix material 40 is then allowed to harden.

Preferably, the matrix material has a relatively low viscosity before hardening so that intimate contact between the matrix material 40 and the appliance 34 is assured. In this manner, the matrix material 40 is able to substantially penetrate in various recesses, cavities and other structural features of the appliance 34 so that a secure connection between the appliance 34 and the matrix material 40 can be established. An example of a suitable matrix material having a relatively low viscosity is a silicone material such as "RTV615" silicone material from General Electric as mentioned above. The relatively low viscosity of this silicone matrix material also assures that the matrix material will assume a configuration that closely matches the shape of the adjacent surfaces of the replica teeth 22.

Alternatively, the matrix material 40 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. If a light-curable adhesive is to be used for bonding the appliances 34 to the patient's teeth, the matrix material 40 is preferably optically clear and transmits actinic radiation without substantial absorption.

Once the matrix material 40 has hardened, the tray 30, together with the matrix material 40 and the appliances 34, are detached from the replica 20. The use of the release agent as mentioned above helps facilitate detaching of the appliances 34 from the corresponding replica teeth 22. Excess material of the tray 30 and excess matrix material 40 is then trimmed as desired and discarded. The resultant trimmed transfer apparatus 44 (comprising the tray 30, the matrix material 40 and the appliances 34) is shown in cross-sectional view in FIG. 7.

Once the patient has returned to the office, the patient's teeth that are to receive appliances are isolated using cheek retractors, tongue guards, cotton rolls, dry angles and/or other articles as needed. The teeth are then thoroughly dried using pressurized air from an air syringe. Etching solution (such as 3M Unitek Transbond XT brand etching gel) is then dabbed onto the teeth in the general area that is to be covered by the appliances 34, taking care to prevent the etching solution from flowing into interproximal contacts or engaging the skin or gingiva.

After the etching solution has remained on the selected tooth surfaces for a period of approximately 30 seconds, the solution is rinsed away from the teeth with a stream of water for 15 seconds. The patient's teeth are then dried by the application of pressurized air from an air syringe (for example, for a time period of 30 seconds) and excess water is removed by suction. Care should also be undertaken to ensure that the saliva does not come in contact with the etched enamel surfaces. Cotton rolls and other absorbent devices are replaced as needed, again making sure that saliva does not contact the etched enamel. Air from the air syringe may then be applied to the teeth again to ensure that the teeth are thoroughly dried.

Figure 7:
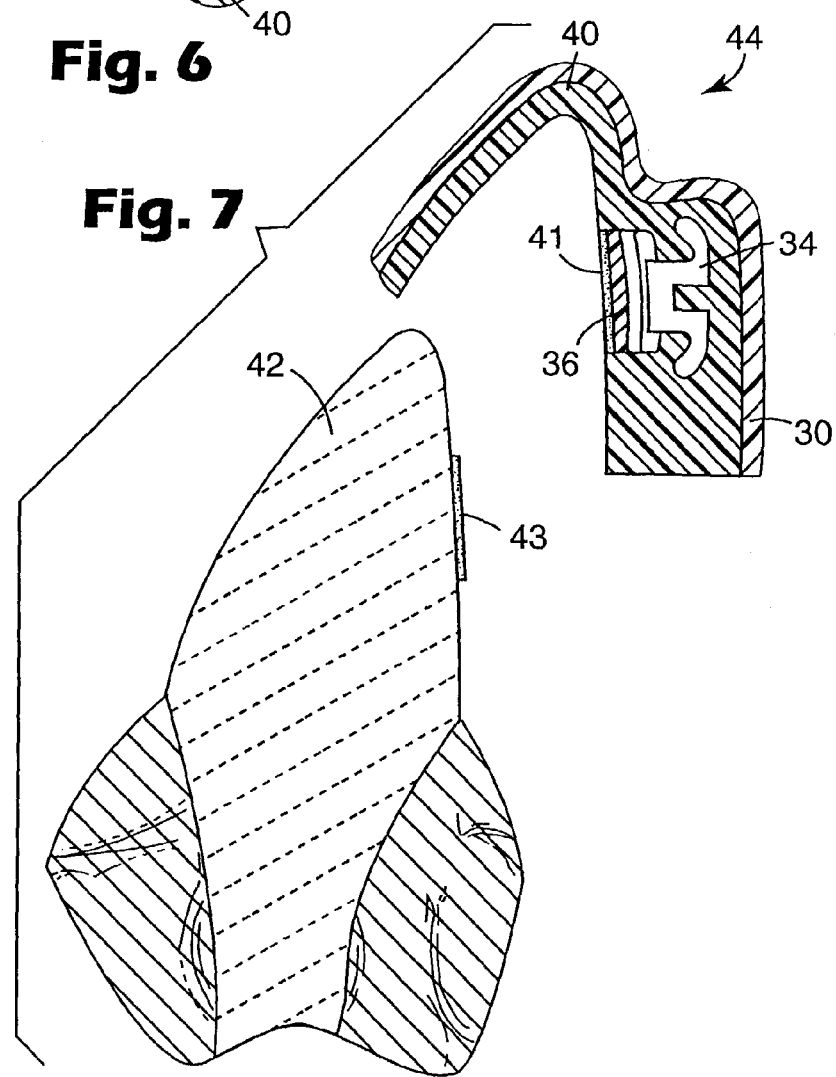
FIG. 7 is an enlarged side cross-sectional view showing the act of applying the transfer apparatus to one of the patient's teeth.

Next, a bonding adhesive is applied to the hardened adhesive 36 and/or the selected areas of the patient's teeth. Optionally, the adhesive is a two-component adhesive as depicted in FIG. 7. For example, the first component 41 is a Transbond brand MIP moisture insensitive primer, and the second component 43 is Transbond brand Plus self-etching primer, both from 3M Unitek. (If a self-etching primer is used, the etching step described earlier is omitted.) The first component 41 is applied to the hardened adhesive 36 and the second component 43 is applied to the area of the patient's tooth that is to receive the appliance 34. In FIG. 7, the patient's tooth is designated by the numeral 42.

After the first component 41 has been applied to the hardened adhesive 36 and the second component 43 has been applied to the corresponding area of the patient's tooth 42, the tray 30 is then positioned over the corresponding teeth and seated, optionally with a swinging, hinge-type motion. Since the shape of the cavity of the matrix material 40 matches the shape of the underlying teeth, the appliances 34 are simultaneously seated against the underlying teeth 42 at precisely the same locations corresponding to the previous position of the appliances 34 on the replica 20. Preferably, pressure is then applied to the occlusal, labial and buccal surfaces of the tray 30 until the bonding adhesive has sufficiently hardened. Optionally, finger pressure may be used to firmly press the appliances 34 against the enamel surfaces of the patient's teeth 42.

Other examples of suitable two-component chemical curing adhesives include Sondhi brand Rapid-Set indirect bonding adhesive, Unite brand adhesive and Concise brand adhesive, all from 3M Unitek. Alternatively, a resin-modified glass ionomer cement may be employed.

Once the bonding adhesive has hardened, the tray 30 is carefully removed from the patient's dental arch. Preferably, the tray 30 is first separated from the matrix material 40, which remains in place over the dental arch along with the appliances 34. Next, the matrix material 40 is detached from the appliances 34. Optionally, a hand instrument such as a scaler may be used to help hold each appliance 34 against the surface of the respective tooth 42 of the patient as the matrix material 40 is peeled away from the appliances 34. However, in instances where a relatively soft matrix material is employed or otherwise readily releases from the appliances 34, the use of a scaler to help avoid fracturing the fresh adhesive bond is optional.

As another option, the tray 30 may be separated from the matrix material 40 before the bonding adhesive has hardened. This option is particularly useful when the bonding adhesive is a light-curable adhesive.

Once the matrix material 40 has been detached from the appliances 34, an archwire is placed in the slots of the appliances 34 and ligated in place. Suitable ligation devices include tiny, elastic O-rings as well as sections of wire that are tied in a loop around the appliances 34. As another option, the appliances 34 may be self-ligating appliances that include a latch for releasably engaging the archwire such as those described in U.S. Pat. No. 6,302,688 and PCT Publication No. WO02/089693.

As can be appreciated, the hardened adhesive 36 provides a "custom" base or bonding surface for the base of the corresponding appliance 34. The configuration of this bonding surface closely matches the shape of the patient's tooth surface and consequently facilitates the subsequent bond (using the bonding adhesive components 41, 43) that is established between the appliance 34 and the tooth 42. The bonding surface reduces the likelihood that the appliance 34 will become unintentionally detached from the tooth during the course of treatment.

The light-transmitting replica 20 provides a number of important advantages. The light-transmitting replica 20 enables actinic radiation to reach all portions of the adhesive 36, including portions near the middle of the appliance base that might otherwise be difficult to reach. As a consequence, all portions of the adhesive 36 are hardened before the appliance 34 is detached from the replica 20 and the configuration of the resulting bonding surface is not disturbed. The resulting bonding surface has a configuration that precisely matches the shape of the corresponding replica surface.

The replica 20 also presents a relatively smooth outer surface, especially when the replica 20 is made of a polymeric material such as epoxy resin. As a consequence, the surface of the replica 20 faithfully represents the shape and texture of the impression and does not introduce any significant amount of additional roughness or texture. Moreover, this smooth surface enables the bonding surface of the hardened adhesive 36 to assume a relatively smooth shape so that a precise, mating fit with the patient's tooth can be attained. As such, the replica 20 need not be coated with a soap solution or wax as described earlier in connection with conventional techniques using stone models which are porous.

The use of the light-transmitting replica 20 is an improvement over techniques using replicas made of materials that are opaque to the transmission of actinic radiation, such as replicas made of plaster of Paris. When an opaque replica is used together with an opaque appliance, portions of adhesive that are located near the center of the appliance base may not sufficiently harden. The unhardened portions of adhesive tend to shift and deform as the appliance is pulled away from the replica and as a result may not retain a shape that matches the configuration of corresponding areas of the replica.

In addition, the unhardened portions found when using an opaque replica as mentioned above may also pull away from adjacent areas of the appliance base as the appliance is detached from the replica. Those portions, even when later hardened under the influence of ambient light, may weaken the bond between the hardened adhesive and the appliance and facilitate unintentional detachment of the appliance during the course of treatment. Also, it has been observed that such unhardened portions present a cloudy appearance, in contrast to the relatively clear appearance of adjacent, hardened portions. It is believed that the cloudy appearance is due to the increased surface roughness of the unhardened portions, as well as to detachment of the adhesive from the appliance base. The cloudy, unhardened portions together with the clear, hardened portions tend to present a somewhat unsightly spotted appearance that is not eliminated even after the unhardened portions cure under the influence of ambient light.

The use of the spacer material 26, 28 in the method described above is a significant advantage in that an appropriate region for receiving matrix material 40 in the tray 30 is provided. The spacer material 26, 28 can be shaped as needed to provide precisely the volume and configuration of region as may be desired. For example, the sheet of spacer material 28 ensures that a uniform thickness of matrix material is subsequently provided around the substantial extent of the tooth 42 with the exception of the areas adjacent the appliance 34.

Moreover, the use of the spacer material 26, 28 facilitates the use of a matrix material having a relatively low viscosity, such as a matrix material having a liquid consistency. The tray 30 is relatively stiff, and consequently maintains its shape during forming of the matrix material 40. As a result, the transfer apparatus 44 is constructed such that the tray 30 does not directly contact the patient's teeth or gingival tissue. Instead, only the matrix material 40 comes into contact with the patient's teeth, so that a close, matching fit with such oral structure is provided.

Another advantage of the present invention is that the relatively soft matrix material 40 is flexible and can accommodate a limited amount of tooth movement. For example, the teeth of the patient may have slightly shifted between the time that the impressions are taken and the time that the transfer apparatus 44 is fitted in the patient's oral cavity for bonding the appliances 34. The matrix material 40 has sufficient flexibility to comply with small shifts or adjustments in the patient's tooth positions, so that the appliances 34 are properly bonded to the intended, pre-determined locations on the patient's tooth.

The matrix material 40 preferably has a viscosity before curing that is less than about 60,000 cp. More preferably, the matrix material 40 has a viscosity before curing that is less than about 25,000 cp. Most preferably, the matrix material 40 has a viscosity before curing that is less than about 8000 cp. Once hardened, the matrix material 40 has a Shore A hardness that is in the range of about 10 to about 80, more preferably in the range of about 30 to about 60 and most preferably in the range of about 40 to about 50.

Furthermore, the use of the spacer material 26, 28 enhances control over construction of the transfer apparatus, including the resultant shape of the tray 30 and the contained matrix material 40. For instance, the sheet of spacer material 28 enables the resultant thickness of the matrix material 40 to be relatively uniform and preferably relatively thin. This uniform thickness of relatively small dimension facilitates curing of a photocurable adhesive used to bond the appliances to the patient's teeth. Specifically, when a light-curable adhesive is used to bond the appliances 34 to the patient's teeth, the uniform thickness of matrix material 40 helps to ensure that the light-curable adhesive beneath each appliance 34 is sufficiently cured to the same extent from one appliance 34 to the next. In this manner, the user need not compensate for varying thicknesses of matrix material and the curing times associated with each quantity of adhesive need not vary from one appliance 34 to the next.

Figure 8:
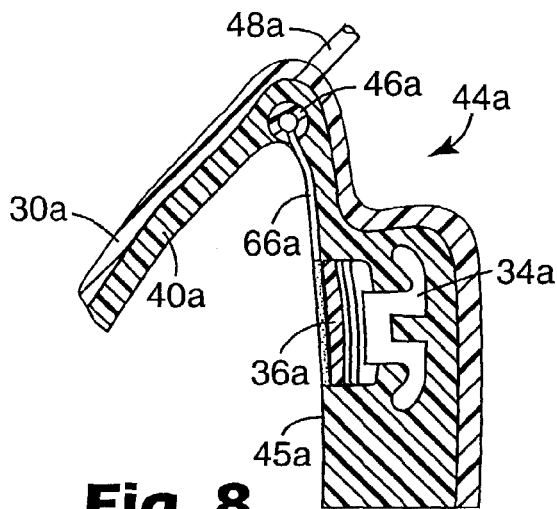
FIG. 8 is an enlarged side cross-sectional view of another transfer apparatus for indirect bonding according to another embodiment of the invention.

A transfer apparatus 44a constructed in accordance with another embodiment of the invention is shown in FIG. 8. The transfer apparatus 44a includes a tray 30a having a channel and a matrix material 40a that is received in the channel. Except as described, the tray 30a and the matrix material 40a are substantially identical to the tray 30 and the matrix material 40 set out above.

The transfer apparatus 44a includes a passageway that extends next to a cavity 45a of the matrix material 40a. The cavity 45a has a configuration matching the replica of the patient's teeth. The passageway in the embodiment shown in FIG. 8 is provided within a length of flexible tubing 46a, although other types of passageways are also possible.

The tubing 46a has a series of small holes that are open to the cavity 45a. The tubing 46a also includes an outlet section 48a that extends through the matrix material 40a and the tray 30a in approximately the mesial-distal center of the transfer apparatus 44a. The ends of the tubing 46a that are located adjacent the distal ends of the cavity 41a are closed.

Preferably, a channel or passage 66a extends from the tubing 46a to the hardened adhesive 36a of each appliance 34a. The passage 66a may be made by placing a length of wire, string or monofilament cord along the replica tooth before placing the matrix material between the tray 30 and the replica tooth. Once the matrix material has hardened, the string or cord is removed, leaving the passage 66a.

The outlet 48a is connected to a source of vacuum. Once the transfer apparatus 44a is placed over the patient's tooth structure during a bonding procedure, the source of vacuum is activated. As vacuum pressure is applied, air is evacuated from the cavity 45a. The resulting negative pressure in the cavity 45a tends to draw the matrix material 40a and the tray 30a toward the patient's tooth structure, such that the appliances (including the appliance 34a) held by the matrix material 40a are firmly pressed against the enamel surfaces of the patient's teeth.

The vacuum is applied to the outlet 48a until such time as the bonding adhesive for bonding the appliances to the patient's teeth has hardened. Subsequently, vacuum pressure is relieved and pressure in the cavity 45a returns to atmospheric pressure. The tray 30a and the matrix material 40a are then removed, leaving the appliances 34a firmly bonded to the patient's teeth.

Figure 9:
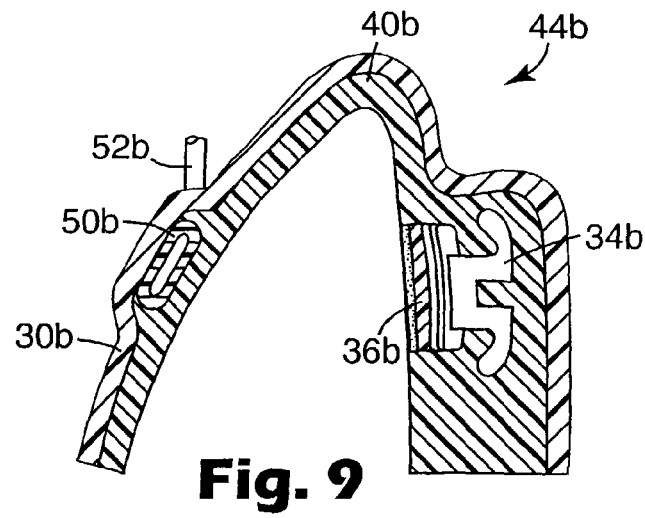
FIG. 9 is a view somewhat similar to FIG. 8 except showing a transfer apparatus in accordance with another embodiment of the invention.

A transfer apparatus 44b according to another embodiment of the invention is illustrated in FIG. 9. Except as described below, the transfer apparatus 44b includes a tray 30b and a matrix material 40b that are essentially identical to the tray 30 and matrix material 40 described above and illustrated in FIGS. 6 and 7.

The transfer apparatus 44b includes one or more bladders 50b that can be pressurized by a fluid such as pressurized air. A cross-sectional view of one bladder 50b is illustrated in FIG. 9. The bladder or bladders are connected by a conduit or passageway to an inlet 52b that, in turn, is detachably connected to a source of fluid such as pressurized air.

The bladder(s) 50b are located between the tray 30b and the matrix material 40b in a location opposite the appliances (such as appliance 34b). During a bonding procedure, pressurized air is admitted through the inlet 52b and directed to the bladder(s) 50b. As the bladder(s) 50b expand, the transfer apparatus 44b is urged in a direction toward the bladder(s) 50b and causes adhesive 36b on the base of the appliances 34b to bear against the adjacent surface of the patient's tooth.

In the illustrated example, a bladder 50b is located along the lingual side of the patient's dental arch when the transfer apparatus is placed in the patient's oral cavity. The appliances 34b are buccolabial appliances adapted for bonding to the buccolabial surfaces of the patient's tooth. As the bladder 50b expands, the transfer apparatus 44b along with the appliances 34b are urged in a lingual direction.

However, the concepts exemplified in FIG. 9 may also be adapted for use in bonding of lingual appliances to lingual surfaces of the patient's teeth. For example, the bladder(s) 50b may extend along the buccolabial side of the patient's dental arch in a position between the matrix material 40b and the tray 30b. The appliances 34b are positioned in the matrix material 40b along the lingual side of the patient's dental arch. As the bladder(s) 50b expand in this example, the transfer apparatus 44b is urged in a buccolabial direction and causes the base of the appliances 34b to firmly bear against the lingual surfaces of the patient's teeth.

In the embodiments of FIGS. 8 and 9, the positive or negative air pressure, in conjunction with the bladder(s) or passageways, tends to firmly hold the base of the appliances in contact with adjacent enamel surfaces of the patient's tooth. Such firm contact facilitates establishing a relatively high bond strength between the appliances and the teeth. In addition, such construction helps resist unintentional movement of the transfer apparatus 44a, 44b as the adhesive is curing, as might otherwise occur if the patient's jaws move or if the transfer apparatus is bumped before the time that the bonding adhesive has sufficiently hardened.

Figure 10:
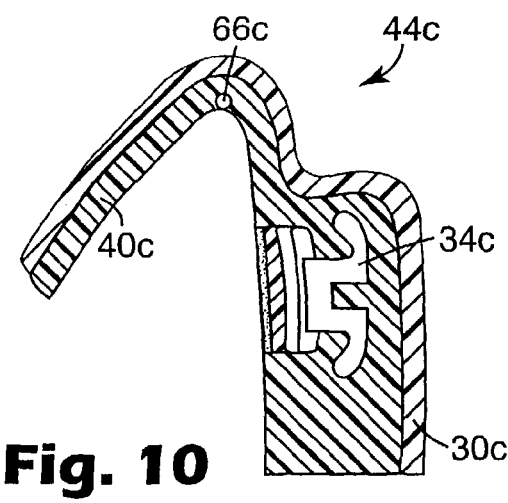
FIG. 10 is a view somewhat similar to FIG. 8 except showing a transfer apparatus according to yet another embodiment of the invention.

A transfer apparatus 44c according to another embodiment of the invention is illustrated in FIG. 10. The transfer apparatus 44c includes a tray 30c and a matrix material 40c. Except as described below, the tray 30c and the matrix material 40c are essentially the same as the tray 30 and matrix material 40 as set out above.

The transfer apparatus 44c includes a cord 66c that is at least partially embedded in the matrix material 40c. Preferably, the cord 66c is elongated and flexible, and optionally is a string made of nylon or other material. The cord 66c generally extends in a direction along the longitudinal axis of the cavity of the matrix material 40c.

The cord 66c facilitates removal of the matrix material from the patient's oral cavity after the bonding procedure is complete. For example, after the tray 30c has been detached from the matrix material 40c, the practitioner may pull on a free end of the cord 66c that extends out of the matrix material 40c. As the cord is pulled, the matrix material fractures along the path of the cord, such that the matrix material 40c is split (or essentially split) into two sections. The two sections can then be easily removed from the oral cavity as desired, reducing the likelihood that the bond between the appliance 34c and the patient's tooth will be disturbed.

Figure 11:
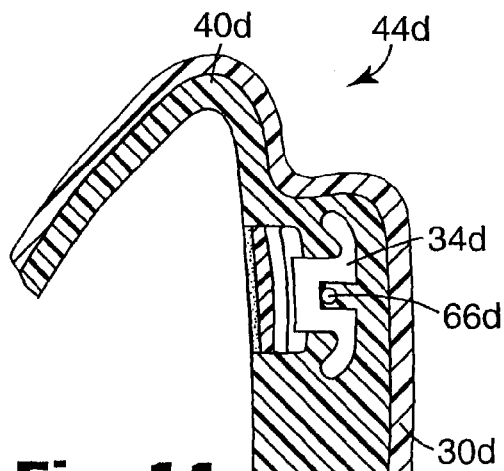
FIG. 11 is a view somewhat similar to FIG. 8 except showing a transfer apparatus in accordance with still another embodiment of the invention.

In the embodiment shown in FIG. 10, the cord 66c extends in the cavity of the matrix material 40c along a path that approximately corresponds to the occlusal edge of the patient's dental arch. The transfer apparatus 44d shown in FIG. 11 is somewhat similar. However, in the transfer apparatus 44d, a cord 66d extends along a location generally corresponding to the intended path of the archwire. Such construction facilitates release of the matrix material 40d from the appliances and may be especially desirable in instance where the appliances are securely connected to the matrix material 40d.

A variety of other embodiments are also possible and will be apparent to those skilled in the art. For example, in the embodiments shown in FIGS. 8–11, the tray may be omitted provided the matrix material has sufficient strength and rigidity. Moreover, the various features described in the figures may be combined with one another.

As another option, the transfer apparatus described in the various embodiments above may be used for bonding appliances such as brackets, tubes and lingual sheaths to the lingual surfaces of the patient's teeth. In that instance, the bladders and cords, if utilized, are adapted and modified as needed.

Additionally, the transfer apparatus may be used for bonding only a single appliance to a patient's tooth. For example, a portion of the transfer apparatus described above may be used to bond a single appliance to a single tooth subsequent to the time that other appliances are bonded, such as in instances where access to the tooth is initially hindered by other teeth. As another example, a portion of the transfer apparatus described above may be used to re-bond an appliance that has unintentionally debonded from the tooth, or to bond a new appliance to a tooth to replace the original appliance.

A number of other variations, modifications and additions are also possible without departing from the spirit of the invention. Accordingly, the invention should not be deemed limited to the specific embodiments described above, but instead only by a fair scope of the claims and their equivalents.

EXAMPLE

A test was conducted to compare the surface roughness of a sample of hardened modeling stone to the surface roughness of a sample of hardened epoxy resin. A stone sample was made by preparing a quantity of Quickstone brand laboratory stone (from Whip Mix Corporation) according to the manufacturer's directions. The stone preparation was then placed in a recess of a polypropylene substrate and allowed to harden.

A surface roughness tester (model no. SJ-301, from Mitutoyo Corporation, Kanagawa, Japan) was used at five distinct locations of the hardened stone to determine surface roughness. At the five locations, the hardened stone had an average surface roughness of 53.16 micro-inch (microinch Ra), with a standard deviation of 4.22.

The surface roughness test was repeated as described above, except that epoxy was used instead of modeling stone. The epoxy was the E-CAST F-82 resin and No. 302 hardener, from United Resin Corporation, as described above. At five locations, the hardened epoxy had an average surface roughness of 11.12 micro-inch, with a standard deviation of 0.93.

The surface roughness test was again repeated to determine the surface roughness of the polypropylene substrate. At five locations, the substrate had an average surface roughness of 9.7 micro-inch, with a standard deviation of 1.64.

The data show that the epoxy exhibited a roughness very similar to the roughness of the casting surface (i.e. the polypropylene substrate), while the stone exhibited a surface roughness that was significantly higher. Consequently, the epoxy material assumed a configuration during casting that closely resembled the surface of the casting surface, while the stone assumed a configuration during casting that was significantly rougher in texture.

The invention claimed is:

1. A method of bonding an orthodontic appliance to a patient's tooth structure comprising:
   providing a positive replica of a patient's tooth structure, wherein the replica is comprised of a material that transmits actinic radiation;
   placing a photocurable composition in a location between the base of an orthodontic appliance and the replica tooth structure;
   directing actinic radiation to the photocurable composition in order to harden the photocurable composition and make a bonding surface, wherein the act of directing actinic radiation to the photocurable composition is carried out by directing at least a portion of the actinic radiation through the replica tooth structure;
   detaching the appliance and the hardened photocurable composition from the replica tooth;
   applying a bonding adhesive to the hardened photocurable composition and/or selected areas of a patient's tooth; and
   hardening the bonding adhesive in order to bond the hardened photocurable composition and the appliance to the patient's tooth.

2. A method of bonding an orthodontic appliance according to claim 1 wherein the material comprises a polymeric material.

3. A method of bonding an orthodontic appliance according to claim 1 wherein the material comprises an epoxy resin.

4. A method of bonding an orthodontic appliance according to claim 1 wherein the photocurable composition is an adhesive.

5. A method of bonding an orthodontic appliance according to claim 1 wherein the photocurable composition begins to harden when exposed to actinic radiation in the visible range.

6. A method of bonding an orthodontic appliance according to claim 1 wherein the appliance is an orthodontic bracket made of a metallic material.

7. A method of bonding an orthodontic appliance according to claim 1 wherein the act of placing a photocurable composition in a location between the base of at least one orthodontic appliance and the replica tooth structure includes the act of placing the photocurable composition on the base of at least one orthodontic appliance and the act of relatively moving each appliance and the replica tooth structure such that the photocurable composition engages the replica tooth structure.

8. A method of bonding an orthodontic appliance according to claim 7 wherein the act of relatively moving each appliance and the replica tooth structure includes the act of moving each appliance while the replica tooth structure is stationary.

9. A method of bonding an orthodontic appliance according to claim 1 wherein the actinic radiation includes radiation in the visible range.

10. A method of bonding an orthodontic appliance according to claim 1 and including the acts of providing at least one additional orthodontic appliance and placing photocurable composition between each additional appliance and the replica tooth structure.

11. A method of orthodontic indirect bonding comprising:
   making a positive replica of a patient's tooth structure, wherein the replica is comprised of a material that transmits actinic radiation;
   placing a photocurable composition in a location between the base of at least one orthodontic appliance and the replica tooth structure;
   directing actinic radiation to the photocurable composition in order to harden the photocurable composition, wherein the act of directing actinic radiation to the photocurable composition is carried out at least in part by directing actinic radiation through the replica of the patient's tooth structure;
   forming a transfer apparatus over each appliance and the replica tooth structure;
   detaching the transfer apparatus, the photocurable composition and each appliance from the replica;
   applying a bonding composition to the hardened photocurable composition and/or selected areas of the patient's teeth; and
   placing the transfer apparatus over the patient's teeth in order to bond the hardened photocurable composition and each appliance to the patient's teeth.

12. A method of orthodontic indirect bonding according to claim 11 wherein the act of forming a transfer apparatus includes the act of providing a matrix material having a Shore A hardness that is in the range of about 10 to about 80.

13. A method of orthodontic indirect bonding according to claim 11 wherein the act of forming a transfer apparatus includes the act of providing a curable matrix material that has a viscosity before curing of less than about 60,000 cp.

14. A method of orthodontic indirect bonding according to claim 11 wherein the act of forming a transfer apparatus includes the act of placing a spacer material over at least a portion of the replica.

15. A method of orthodontic indirect bonding according to claim 14 wherein the act of forming a transfer apparatus over each appliance and replica tooth structure is carried out by forming at least a portion of the transfer apparatus over the spacer material.

16. A method of orthodontic indirect bonding according to claim 11 wherein the replica material is comprised of a polymeric material.

* * * * *